(12) United States Patent
Lee et al.

(10) Patent No.: US 9,170,261 B2
(45) Date of Patent: Oct. 27, 2015

(54) PEPTIDE SPECIFIC FOR OVARIAN CANCER AND APPLICATIONS

(71) Applicant: National Tsing Hua University, Hsinchu (TW)

(72) Inventors: Gwo-Bin Lee, Hsinchu (TW); Chih-Hung Wang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 60 days.

(21) Appl. No.: 14/185,108

(22) Filed: Feb. 20, 2014

(65) Prior Publication Data

US 2015/0111227 A1 Apr. 23, 2015

(30) Foreign Application Priority Data

Oct. 17, 2013 (TW) .............................. 102137462 A

(51) Int. Cl.
| | | |
|---|---|---|
| C07K 17/14 | (2006.01) | |
| G01N 33/574 | (2006.01) | |
| G01N 33/543 | (2006.01) | |
| C07K 7/08 | (2006.01) | |

(52) U.S. Cl.
CPC ............ *G01N 33/57449* (2013.01); *C07K 7/08* (2013.01); *G01N 33/54326* (2013.01)

(58) Field of Classification Search
None
See application file for complete search history.

(56) References Cited

U.S. PATENT DOCUMENTS 8,624,008 B2    1/2014  Lee et al.
2010/0172864 A1* 7/2010  Arap et al. ................... 424/85.2

* cited by examiner

*Primary Examiner* — Brad Duffy
*Assistant Examiner* — Nelson B Moseley, II
(74) *Attorney, Agent, or Firm* — WPAT, P.C.; Anthony King

(57) ABSTRACT

The present invention provides a novel peptide with high specificity for recognition of ovarian cancer. The peptide is selected using M13 phage display library and epithelial-enrich-conjugated magnetic beads. Only a small amount of the peptide is required to establish over 80% binding activity to ovarian cancer comparing to low binding activities to other cancers, showing high specificity for ovarian cancer. Thus the peptide of the present invention can be effective in early detection of ovarian cancer.

10 Claims, 2 Drawing Sheets

(A)

(B)

(C)

(D)

PEPTIDE SPECIFIC FOR OVARIAN CANCER AND APPLICATIONS

CROSS-REFERENCES TO RELATED APPLICATIONS

This application claims priority to Taiwan Patent Application No. 102137462 filed on 17 Oct. 2013. All disclosure of which is incorporated herein by reference in its entirety.

BACKGROUND OF THE INVENTION

1. Field of the Invention

The present invention is related to a novel peptide specific for ovarian cancer and the applications thereof.

2. The Prior Arts

Ovary is the reproductive organ found in female individuals. The major functions of the ovary are making and storing ova, producing hormones such as estrogen and progesterone, which provide the ability of reproduction and support the development of womb and vagina. When the tissues of ovary establish malignant transformation, for instance, abnormal cell division and formation of tumor, it is diagnosed as ovarian cancer. Ovarian cancer is one of the most common cancers in obstetrics and gynecology, which is only next to cervical cancer and takes the second place of the most common cancer among Taiwanese female population. Ovarian cancer can develop in female of all age groups, and the incidence increases with age. Epithelial ovarian cancer is more likely to be found in women over 40 years old, while malignant ovarian germ cell tumor often is diagnosed in patients under 20. Most ovarian cancers are not easily to be diagnosed due to their insignificant early symptoms. Only when the tumor enlarged in late stages which suppress the large intestine and result in conditions such as constipation, diarrhea, nausea, and flatulence, can the tumor be discovered. The 5-year survival rate in early stage ovarian cancer is up to 70-90% comparing to only 20-50% in late stage ovarian cancer; hence, being possible to discover ovarian in its early stage can largely increase the chance of recovery and survival.

Currently, clinical ovarian cancer detection method includes cavum pelvis examination, which is able to detect the existence of tumor but unable to distinguish its characteristics, thus, lacking specificity and sensitivity as means of cancer screening. Ultrasonic examination like virginal ultrasonic examination and Doppler ultrasound examination are able to tell the vascular distribution and blood flow of the tumor; however, due to the fact that ovary with ovarian cancer is similar to a normal one in size and appearance, such ultrasonic examinations still lack reliability. Serum tumor makers such as CA-125, CA-199, Carcinoembryonic antigen (CEA), lysophosphatidic acid (LPA), α-fetoprotein (α-FP), human chorionic gonadotropin (hCG), inhibin, Mullerian inhibiting substance, although, can be used to screen for early stage ovarian cancer; however, most serum tumor makers exhibit relatively poor detecting ability for early stage tumor comparing to tumor that reoccurred after surgery.

Thus, the public still need a practice or an examination that can be used as early ovarian cancer screening so far, and developing serum tumor marker with high specificity for clinical application is necessary since it can not only serve as rapid detection for early stage ovarian cancer but also increase the survival rate of prognosis.

SUMMARY OF THE INVENTION

As a result, the present invention provides an isolated ovarian cancer-targeting peptide, comprising an amino acid sequence of SEQ ID NO: 1 encoded by a nucleotide sequence of SEQ ID NO: 2, wherein the peptide is conjugated to a magnetic particle.

Another aspect of the present invention is to provide a method of detecting or diagnosing ovarian cancer in a subject, comprising contacting a sample from the subject with the peptide of the present invention under a condition, wherein the condition allows the peptide to connect to an ovarian cancer cell. The method further comprising conjugating a plurality of the peptides of the present invention to a magnetic particle to form a peptide-magnetic particle complex, wherein the magnetic particle is a magnetic bead. In one embodiment of the present invention, the binding activity of the peptide to the ovarian cancer cell is at least 80%, wherein the condition is the peptide concentration of 10 pg/mL to 10 µg/mL, preferably, 10 pg/mL. According to the method of the present invention, the peptide is conjugated to a detectable label, wherein the detectable label is a fluorophore, a chemiluminophore, a radioactive isotope, an enzyme, or a biotin.

Another aspect of the present invention is to provide a microfluidic chip, comprising the ovarian cancer-targeting peptide of the present invention.

The present invention use M13 phage display library and epithelial-enrich-conjugated magnetic beads to obtain a novel peptide, and only an extreme small amount of the peptide is required to achieve significant ovarian cancer binding activity with high specificity, thus, is particularly useful for rapid cancer screening. Moreover, the peptide of the present invention shows negligible binding activity to other cancers such as pancreatic cancer, colorectal cancer, cervical cancer, or liver cancer; hence the peptide of the present invention recognizes ovarian cancer with high specificity and is able to be used effectively in early detection of ovarian cancer so as to enhance the recovery and survival rate.

The present invention is further explained in the following embodiment illustration and examples. Those examples below should not, however, be considered to limit the scope of the invention, it is contemplated that modifications will readily occur to those skilled in the art, which modifications will be within the spirit of the invention and scope of the appended claims.

DETAILED DESCRIPTION OF THE PREFERRED EMBODIMENT

Figure 1:
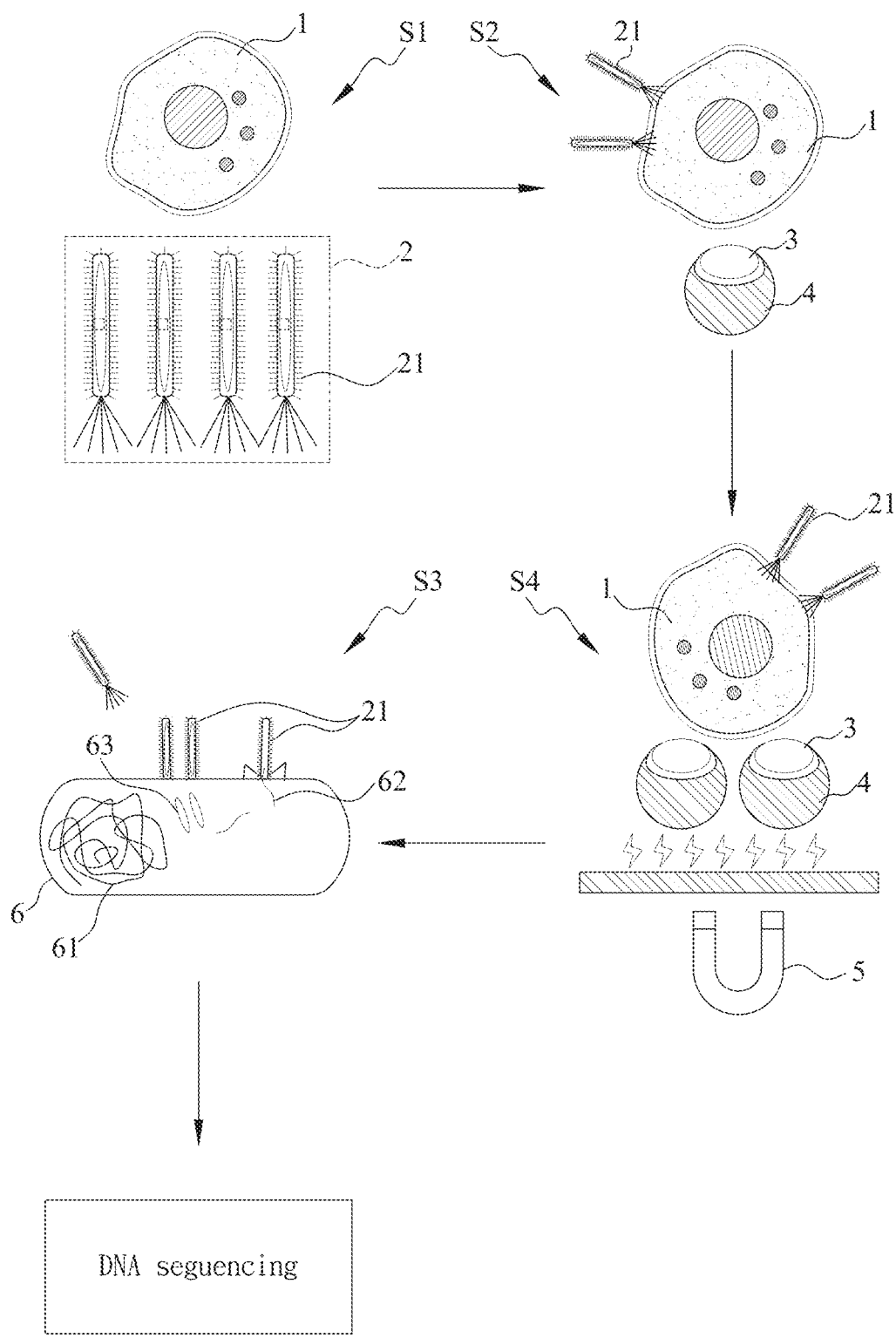
FIG. 1 is a flowchart illustrating an embodiment of a process for the selection of a tumor marker in ovarian cancer using the combination of microfluidic chip and M13 phage display library.

The present invention relates to an ovarian cancer-targeting peptide selected by using a process of the combination of a M13 phage display library, epithelial-enrich-conjugated magnetic beads and microfluidic chip technology. The ovarian cancer-targeting peptide selected establishes high specificity and high binding activities. Furthermore, the peptide in different concentration is conjugated to magnetic beads to detect the high binding activities to ovarian cancer cell; various types of cancer cells are incubated with magnetic beads conjugated with the peptide of the present invention to confirm the high specificity of the ovarian cancer-targeting peptide.

Definition

As used herein, the terms "polynucleotide", "nucleic acid", "nucleic acid molecule", "nucleic acid sequence", "polynucleotide sequence", and "nucleotide sequence" are interchangeable to refer to polymeric forms of nucleotides of any length. The polynucleotides can comprise deoxyribonucleotides, ribonucleotides, and/or their analogs or derivatives. Nucleotide sequences shown herein are listed in the 5' to 3' direction.

The terms "peptide", "peptide" and "protein" are used interchangeably herein, refer to a polymeric form of amino acids of any length.

A peptide is "specific for an ovarian cancer" or "ovarian cancer-targeting peptide" when the peptide binds to or interact with ovarian cancer but does not bind to or interact significantly with other cancers or cells.

A "sample" is any biological specimen derived from a patient. The term includes, but is not limit to, biological fluids such as blood, serum, plasma, urine, cerebrospinal fluid, tears, saliva, lymph, dialysis fluid, lavage fluid, semen, and other liquid samples, as well as cells and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization; or enrichment for certain components, such as polynucleotides or polypeptides. Also included in the term are derivatives and fractions of patient samples. A patient sample may be used in a diagnostic, prognostic, or other monitoring assay. The term also applies to a biological specimen from a non-human mammal. The specimen can be from a human patient or a non-human mammal.

As used herein, "cancer" is any abnormal cell or tissue growth, for example, a tumor, whether malignant, pre-malignant, or nonmalignant. It is characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and mucinous cystadenoma. The term cancer includes ovarian cancer, colon cancer, cervical cancer, liver cancer, and pancreatic cancer.

The terms "detectable label", "label", "marker", "tag" as used interchangeably herein, refer to the peptide of the present invention may be conjugated to an atom or molecule such as, but not limited to, FITC, biotin, and radioisotopes, including, but not limited to $^{64}Cu$, $^{67}Cu$, $^{90}Y$, $^{99m}Tc$, $^{111}In$, $^{124}I$, $^{125}I$, $^{131}I$, $^{137}Cs$, $^{186}Re$, $^{211}At$, $^{212}Bi$, $^{213}Bi$, $^{223}Ra$, $^{241}Am$, and $^{244}Cm$, enzymes having detectable products (for example, luciferase, peroxidase, alkaline phosphatase, β-galactosidase, and the like), fluorescers and fluorescent labels, electrochemilluminescent compounds, chemiluminescent compounds, for example, luminol, isoluminol, or acridinium salts.

As used herein, the terms "microfluidic chip," "integrated microfluidic chip," and "chip," are used interchangeably herein to refer to a single integral unit that has a micro fluidic reactor, one or more microfluidic flow channel(s), and one or more valve(s). Microfluidic chips typically also have other microfluidic components, such as pumps, columns, mixers, and the like. Most often the chip is fabricated from elastomer, glass, or silicon. Typically, the chip is box-shaped with a height that is relatively small compared to length and width; however, the chip can have other shapes including cubical, cylindrical, and others.

Preparation of the Peptide Specific for Ovarian Cancer

The peptide of the present invention can be produced using methods known in the art. Cell-based methods and cell-free methods are suitable for producing peptide of the present invention. Cell-based methods generally involve introducing a nucleic acid into a host cell in vitro and culturing the host cell under conditions suitable for expression, then harvesting the peptide, either from the culture medium or from the host cell, for example by disrupting the host cell, or both. Suitable host cells include prokaryotic or eukaryotic cells, including, for example, bacterial, yeast, fungal, plant, insect, and mammalian cells.

The present invention also provides methods of producing a peptide using cell-free in vitro transcription/translation methods, which are well known in the art.

Additionally, peptide moieties and/or purification tags may be added to the peptides. Such regions may be removed prior to final preparation of the polypeptide. The additions of peptide moieties to polypeptides to engender secretion or excretion, to improve stability, and to facilitate purification, among other reasons, are familiar and routine techniques in the art. Suitable purification tags include, for example, V5, polyhistidines, avidin, and biotin. Conjugation of peptides to compounds such as biotin can be accomplished using techniques well known in the art. The peptides can also be conjugated to fluorescent label, chemiluminescent label, radioactive isotope, and enzymatic label according to techniques known in the art.

The peptide of the present invention can also be chemically synthesized using techniques known in the art. For example, a polypeptide corresponding to a fragment of a polypeptide can be synthesized by use of a peptide synthesizer or through the use of solid-phase methods known in the art.

The polypeptides of the disclosure can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography (HPLC) is employed for purification in the present invention. Well known techniques for refolding protein may be employed to regenerate active conformation when the polypeptide is denatured during isolation and/or purification.

Diagnostic Methods

Detection of biomarkers specific for particular diseases provides an effective screening strategy. Early detection can not only provide early diagnosis, but also in the case of cancer, the ability to screen for polymorphisms and detect post-operative residual tumor cells and occult metastases, an early indicator of tumor recurrence. Early detection of disease-specific biomarkers can thus improve survival in patients before diagnosis, while undergoing treatment, and while in remission.

The peptide of the present invention can be used for the diagnosis of ovarian cancer. The peptide of the present invention can be used as diagnostics in many ways, including but not limited to ELISA, Western blot, fluorescence, immunofluorescence, immunohistochemistry, or autoradiography.

Example 1

Screening of Tumor Marker Specific for Ovarian Cancer Cell by Microfluidic Chip and M13 Phage Display Library A. Cell Line and Cell Culture Human ovarian cancer cell line, BG1, was used. BG1 was cultured in DMEM/F12 medium containing 10% Fetal Bovine Serum (FBS). Other conditions of the culture are 37° C. and 5% $CO_2$ in moisture atmosphere.

Other cell lines were used in the embodiments of the present invention including pancreatic cancer cell line (BxPC3), colon cancer cell line (HCT8), cervical cancer cell line (HeLa), and liver cancer cell line (HepG2).

B. Isolation of Phage Bound to BG1 Cells

FIG. 1 is a flowchart illustrating an embodiment of a process for the selection of a tumor marker in ovarian cancer using the combination of microfluidic chip system and M13 phage display library. For the selection of specific tumor markers, firstly, M13 phage display library 2 and ovarian cancer cells 1 were co-incubated at 37° C. and 5% $CO_2$ in moisture atmosphere for 30 minutes (S1); then, after the M13 phage 21 in the library 2 connecting to ovarian cancer cells 1, they were captured by magnetic beads 4 which conjugated with epithelial-enrich 3 (S2) to form a complex; the complex of M13 phage 21, ovarian cancer cell 1, and epithelial-enrich-conjugated bead was captured by a magnet 5 (DynaMagtm-2, Invitrogen co., USA) and were incubated with *Escherichia coli* 6 in lysogeny broth (LB) at 37° C. and normal atmospheric conditions for 16 hours while the mobilized M13 phage or M13 phage with low affinity were washed using sterile deionized water (S3); the phage 21 then attached to *E. coli* 6 in which it injected its linear DNA 62 into the cytoplasm of the *E. coli* 6, after the *E. coli* 6 replicating the phage linear DNA 62 using its own genetic materials 61, the replicated circular DNA 63 fused back to the phage attached and released from the *E. coli* 6 (S4); the DNA of the released phages were then cloned using pCR®2.1-TOPO® vector (Invetrogen co., USA) and were sequenced using M13 reverse primer (5'-caggaaacagctatgac-3') (SEQ ID NO: 3). Please refer to U.S. Pat. No. 8,624,008 issued on 7 Jan. 2014 for details regarding the construction of M13 phage display library, the preparation of magnetic beads, and the preparation of microfluidic chip.

Please refer to FIG. 1, after 5 to 6 selection cycles, the selected M13 phages were collected for cloning and sequencing. The nucleotide sequence of the highest occurrence (16.53%) were discovered from the result of the sequencing: 5'-atgccgcatcctacgaagaattttgatttgtatgtg-3' (SEQ ID NO: 2). The peptide expressed by said nucleotide sequence is N'-MPHPTKNFDLYV-C' (SEQ ID NO: 1), which is the peptide specific for ovarian cancer of the present invention.

Example 2

The Specificity of the Peptide of the Present Invention to Ovarian Cancer

Figure 2:
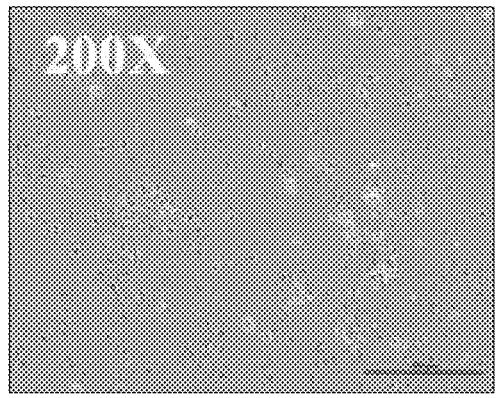
FIG. 2 shows specific binding activities of cancer-targeting peptides with different concentration, conjugated to magnetic beads, to ovarian tumor of microscopy images. (A) magnetic beads without peptide conjugation; (B) magnetic beads conjugated to 10 µg/mL of peptide; (C) magnetic beads conjugated to 10 ng/mL of peptide; (D) magnetic beads conjugated to 10 pg/mL of peptide.
Figure 2:
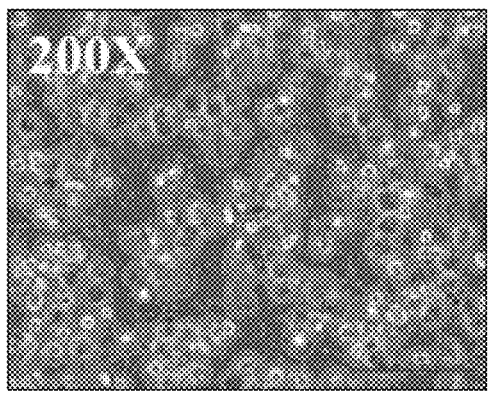
Figure 2:
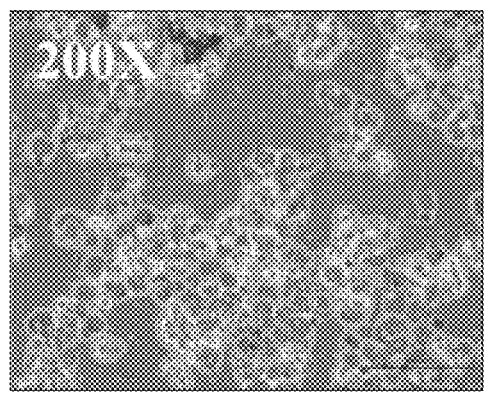
Figure 2:
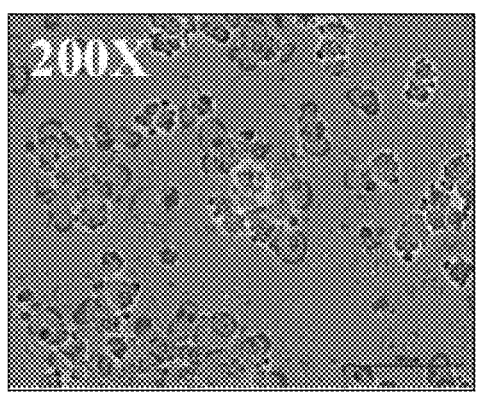

FIG. 2 shows specific binding activities of cancer-targeting peptides with different concentration, conjugated to magnetic beads, to ovarian tumor of microscopy images. Different concentrations of the peptide of the present invention were conjugated to magnetic beads, wherein said concentrations are 10 μg/mL, 10 ng/mL, and 10 pg/mL. The capturing test was performed using $10^5$ ovarian cancer cells.

Under microscopic observation, each concentration of the peptide of the present invention is able to connect to ovarian cancer cells. The result also indicates that only 10 pg/mL of the peptide of the present invention is required to efficiently capture ovarian cancer cells, thus, establishing high specificity of the peptide of the present invention to ovarian cancer cells.

Example 3

The Binding Activity of the Peptide of the Present Invention to Ovarian Cancer Cells 10 ng/mL of the peptide SEQ ID NO:1 of the present invention was used to examine the binding activity to different cancer cells, including pancreatic cancer cell line (BxPC3), colon cancer cell line (HCT8), cervical cancer cell line (HeLa), and liver cancer cell line (HepG2). The result is shown in Table 1.

TABLE 1

Comparison of the binding activity of the peptide of present invention to different cancer cells

| Cell line | Cancer | Connectivity (%) |
|---|---|---|
| BG1 | Overian cancer | 80.38 ± 2.69 |
| BxPC3 | Pancreatic cancer | 12.89 ± 0.21 |
| HCT8 | Colon cancer | 22.37 ± 1.89 |
| HeLa | Cervical cancer | 26.02 ± 2.01 |
| HepG2 | Liver cancer | 15.77 ± 5.25 |

The result above indicates that the peptide of the present invention establishes high binding activity to ovarian cancer cells, which is about 80% comparing to the average connectivity of about 20% to other cancer cells.

In summary, the present invention provides a peptide having more than 80% binding activity to ovarian cancer, which is significantly higher than the average connectivity of about 20% to other cancers. Furthermore, only a small amount of peptide (in the scale of pg/mL) is required to achieve efficient connection, showing that the peptide of the present invention has high specificity to ovarian cancer cells; hence, the peptide of the present invention is suitable for the use of rapid ovarian cancer detection.

What is claimed is:

1. An isolated ovarian cancer-targeting peptide, comprising an amino acid sequence of SEQ ID NO: 1 encoded by a nucleotide sequence of SEQ ID NO: 2.

2. The peptide according to claim 1, wherein the peptide is conjugated to a magnetic particle.

3. A method of detecting or diagnosing ovarian cancer in a subject, comprising contacting a sample from the subject with the peptide according to claim 1 under a condition, wherein the condition allows the peptide to connect to an ovarian cancer cell.

4. The method according to claim 3, further comprising conjugating a plurality of the peptides to a magnetic particle to form a peptide-magnetic particle complex.

5. The method according to claim 4, wherein the magnetic particle is a magnetic bead.

6. The method according to claim 5, wherein the binding activity of the peptide to the ovarian cancer cell is at least 80%.

7. The method according to claim 5, wherein the condition is the peptide concentration of 10 pg/mL to 10 μg/mL.

8. The method according to claim 5, wherein the condition is the peptide concentration of 10 pg/mL.

9. The method according to claim 5, wherein the peptide is conjugated to a detectable label, and the detectable label is a fluorophore, a chemiluminophore, a radioactive isotope, an enzyme, or a biotin.

10. A microfluidic chip, comprising the ovarian cancer-targeting peptide according to claim 1.

* * * * *

SEQUENCE LISTING

<160> NUMBER OF SEQ ID NOS: 3

<210> SEQ ID NO 1
<211> LENGTH: 12
<212> TYPE: PRT
<213> ORGANISM: Artificial sequence

```
-continued

<220> FEATURE:
<223> OTHER INFORMATION: Synthetic peptide

<400> SEQUENCE: 1

Met Pro His Pro Thr Lys Asn Phe Asp Leu Tyr Val
1               5                   10

<210> SEQ ID NO 2
<211> LENGTH: 36
<212> TYPE: DNA
<213> ORGANISM: Artificial sequence
<220> FEATURE:
<223> OTHER INFORMATION: Synthetic nucleotide

<400> SEQUENCE: 2
atgccgcatc ctacgaagaa ttttgatttg tatgtg                                 36

<210> SEQ ID NO 3
<211> LENGTH: 17
<212> TYPE: DNA
<213> ORGANISM: Artificial sequence
<220> FEATURE:
<223> OTHER INFORMATION: Synthetic primer

<400> SEQUENCE: 3
caggaaacag ctatgac                                                      17
```